US009907884B2

(12) United States Patent
Peters et al.

(10) Patent No.: US 9,907,884 B2
(45) Date of Patent: Mar. 6, 2018

(54) BIODEGRADABLE COMPOSITE MATERIAL

(75) Inventors: Fabian Peters, Mannheim (DE); Wolf-Dietrich Huebner, Frankfurt am Main (DE); Christiane Hoffmann, Frankfurt am Main (DE); Nikica Andic, Frankfurt am Main (DE); Kathleen Hasanovic, Frankfurt am Main (DE); Tilo Hniopek, Frankfurt am Main (DE)

(73) Assignee: CURASAN AG, Kleinostheim (DE)

( * ) Notice: Subject to any disclaimer, the term of this patent is extended or adjusted under 35 U.S.C. 154(b) by 196 days.

(21) Appl. No.: 14/122,724

(22) PCT Filed: May 31, 2012

(86) PCT No.: PCT/EP2012/002309
§ 371 (c)(1),
(2), (4) Date: Feb. 28, 2014

(87) PCT Pub. No.: WO2012/163532
PCT Pub. Date: Dec. 6, 2012

(65) Prior Publication Data
US 2014/0170202 A1 Jun. 19, 2014

Related U.S. Application Data

(60) Provisional application No. 61/491,480, filed on May 31, 2011.

(30) Foreign Application Priority Data

May 31, 2011 (EP) .................... 11004466

(51) Int. Cl.
*A61L 27/58* (2006.01)
*A61L 27/56* (2006.01)
*A61L 27/10* (2006.01)
*A61L 27/24* (2006.01)
*A61L 27/12* (2006.01)
*A61L 27/02* (2006.01)
*A61L 31/12* (2006.01)
*A61L 27/42* (2006.01)
*B29C 44/02* (2006.01)

(52) U.S. Cl.
CPC ............. *A61L 27/56* (2013.01); *A61L 27/42* (2013.01); *A61L 27/425* (2013.01); *B29C 44/02* (2013.01); *A61L 2430/02* (2013.01)

(58) Field of Classification Search
CPC ... A61K 9/0024; A61L 2430/02; A61L 27/56; A61L 27/58; A61L 27/46; A61L 27/12; A61L 27/24; A61L 27/10; A61L 2300/604
See application file for complete search history.

(56) References Cited

U.S. PATENT DOCUMENTS

| 4,192,021 | A | 3/1980 | Deibig et al. ............. 623/23.61 |
| 4,373,217 | A | 2/1983 | Draenert .................... 623/23.62 |
| 4,629,464 | A * | 12/1986 | Takata et al. ............. 623/23.61 |
| 4,795,467 | A | 1/1989 | Piez et al. ..................... 424/423 |
| 5,071,436 | A | 12/1991 | Huc et al. ..................... 424/423 |
| 5,650,108 | A | 7/1997 | Nies et al. ..................... 264/122 |
| 5,814,681 | A | 9/1998 | Hino et al. ..................... 523/113 |
| 6,281,271 | B1 | 8/2001 | Rumphorst .................... 523/211 |
| 6,340,648 | B1 | 1/2002 | Imura et al. .................... 501/80 |
| 7,189,263 | B2 | 3/2007 | Erbe et al. .................. 623/23.51 |
| 7,544,212 | B2 | 6/2009 | Li et al. ..................... 623/23.51 |
| 2002/0120033 | A1 | 8/2002 | Jia et al. ........................ 523/115 |
| 2002/0133238 | A1 | 9/2002 | Czernuszka et al. ........... 623/32 |
| 2003/0009235 | A1 | 1/2003 | Manrique et al. ......... 623/23.63 |
| 2004/0175430 | A1 | 9/2004 | Berger et al. ................. 424/602 |
| 2004/0220680 | A1* | 11/2004 | Yamamoto ............... A61F 2/28 623/23.51 |
| 2004/0228927 | A1 | 11/2004 | Berger et al. ................. 424/602 |
| 2004/0235637 | A1 | 11/2004 | Berger et al. .................... 501/72 |
| 2005/0031704 | A1* | 2/2005 | Ahn ........................ A61K 33/42 424/602 |
| 2005/0159820 | A1 | 7/2005 | Yoshikawa et al. ......... 623/23.5 |
| 2006/0172918 | A1 | 8/2006 | Sotome et al. ............... 424/423 |
| 2007/0218098 | A1* | 9/2007 | Reif ........................ A61F 2/28 424/423 |
| 2007/0254011 | A1* | 11/2007 | Schnabelrauch ... A61L 24/0036 424/426 |
| 2008/0069852 | A1* | 3/2008 | Shimp ................... A61L 27/446 424/423 |
| 2008/0187571 | A1 | 8/2008 | Clineff et al. ................ 424/426 |
| 2009/0110743 | A1* | 4/2009 | Dalal et al. ................... 424/499 |
| 2009/0269387 | A1* | 10/2009 | Zubery ................... A61L 27/48 424/423 |
| 2011/0159057 | A1* | 6/2011 | Da Silva Santos ... A61L 27/425 424/400 |
| 2011/0237704 | A1* | 9/2011 | Guelcher et al. ............. 523/115 |

FOREIGN PATENT DOCUMENTS

| DE | 3414924 A1 | 10/1985 |
| DE | 3717818 A1 | 12/1987 |
| DE | 3784646 T2 | 6/1993 |
| DE | 4222763 A1 | 1/1994 |
| DE | 69403439 T2 | 10/1997 |
| DE | 29922585 U1 | 8/2000 |
| DE | 199 39 403 A1 | 2/2001 |
| DE | 100 60 036 C1 | 8/2002 |
| DE | 102005034421 A1 | 5/2006 |
| DE | 102006026000 A1 | 2/2008 |

(Continued)

OTHER PUBLICATIONS

Merriam-Webster Online Dictionary "Prevent" http://www.merriam-webster.com/dictionary/prevent.

(Continued)

*Primary Examiner* — Tracy Liu
(74) *Attorney, Agent, or Firm* — Licata & Tyrrell P.C.

(57) ABSTRACT

The invention relates to a biologically degradable composite material and to a process for the preparation thereof. The biologically degradable composite material according to the invention is preferably a bone reconstruction material which can be used in the field of regenerative medicine, especially as a temporary bone defect filler for bone regeneration.

16 Claims, 2 Drawing Sheets

(56) References Cited

FOREIGN PATENT DOCUMENTS

| | | |
|---|---|---|
| EP | 0164483 A1 | 12/1985 |
| EP | 0243178 A2 | 10/1987 |
| EP | 0267624 A2 | 5/1988 |
| EP | 0302847 A2 | 2/1989 |
| EP | 0309241 A2 | 3/1989 |
| EP | 0386253 | 9/1990 |
| EP | 0932373 | 8/1999 |
| EP | 0941130 | 9/1999 |
| EP | 0984745 A1 | 3/2000 |
| EP | 1150726 A1 | 11/2001 |
| EP | 1270025 A2 | 1/2003 |
| EP | 1372748 A2 | 1/2004 |
| EP | 1413321 A2 | 4/2004 |
| EP | 1413323 A2 | 4/2004 |
| EP | 1719531 A2 | 11/2006 |
| EP | 1891984 A1 | 2/2008 |
| JP | 01-107769 | 4/1989 |
| JP | 05-237178 | 9/1993 |
| WO | WO 87/00058 | 1/1987 |
| WO | WO 89/09787 | 10/1989 |
| WO | WO 89/09788 | 10/1989 |
| WO | WO 90/00892 | 2/1990 |
| WO | WO 94/01063 | 1/1994 |
| WO | WO 94/15653 | 7/1994 |
| WO | WO 96/39202 | 12/1996 |
| WO | WO 98/10712 | 3/1998 |
| WO | WO 98/17330 | 4/1998 |
| WO | WO 98/19718 | 5/1998 |
| WO | WO 98/22154 | 5/1998 |
| WO | WO 98/52498 | 11/1998 |
| WO | WO 00/45871 | 8/2000 |
| WO | WO 02/22045 A1 | 3/2002 |
| WO | WO 02/051449 A2 | 7/2002 |
| WO | WO 02/070029 A2 | 9/2002 |
| WO | WO 03/022319 A1 | 3/2003 |
| WO | WO 03/071991 A1 | 9/2003 |
| WO | WO 03/082365 A1 | 10/2003 |
| WO | WO 2004/112855 A2 | 12/2004 |
| WO | WO 2005/051447 A1 | 6/2005 |
| WO | WO 2006/031196 A1 | 3/2006 |
| WO | WO 2006/056391 A2 | 6/2006 |
| WO | WO 2006/082442 A1 | 8/2006 |
| WO | WO 2006/095154 A2 | 9/2006 |
| WO | WO 2008/028466 A2 | 3/2008 |
| WO | WO 2009/000445 A1 | 12/2008 |
| WO | WO 2010/021559 A1 | 2/2010 |

OTHER PUBLICATIONS

Merriam-Webster Online Dictionary "Prophylaxes" http://www.merriam-webster.com/dictionary/prophylaxis.

Wikipedia, the free encyclopedia "BET Theory" http://en.wikipedia.org/wiki/BET_theory.

Wikipedia, the free encyclopedia "Chlorophyll" http://en.wikipedia.org/wiki/Chlorophyll.

Office Communication dated Mar. 23, 2010 from U.S. Appl. No. 10/580,549, filed Apr. 3, 2007.

Office Communication dated Dec. 7, 2010 from U.S. Appl. No. 10/580,549, filed Apr. 3, 2007.

Office Communication dated Apr. 12, 2011 from U.S. Appl. No. 10/580,549, filed Apr. 3, 2007.

Grynpas, M. "Age and Disease-Related Changes in the Mineral of Bone" Calcified Tissue International 1993 53 (Supplement 1):S57-S64.

González et al. "Effect of Size, Concentration, Surface Area, and Volume of Polymethylmethacrylate Particles on Human Macrophages in vitro" Journal of Biomedical Materials Research 1996 30:463-473.

Palm, F. "Cerasorb° M—A New Synthetic Pure-Phase β-TCP Ceramic Material in Oral and Maxillofacial Surgery" Implants International Magazine of Oral Implantology 2006 vol. 7 Issue 3.

Peters, F. and Reif, D. "Functional Materials for Bone Regeneration from Beta-Tricalcium Phosphate" Mat.-wiss. u. Werkstofftech 2004 35(4):203-207.

Rodrigues et al. "Characterization of a Bovine Collagen-Hydroxyapatite Composite Scaffold for Bone Tissue Engineering" Biomaterials 2003 24:4987-4997.

Urist, M.R. "Bone: Formation by Autoinduction" Science 1965 150:893-899.

Wahl, D.A. and Czernuszka, J.T. "Collagen-Hydroxyapatite Composites for Hard Tissue Repair" European Cells and Materials 2006 11:43-56.

Hirota et al. "Combination with Allogenic Bone Reduces Early Absorption of β-tricalcium Phosphate (β-TCP) and Enhances the Role as a Bone Regeneration Scaffold. Experimental Animal Study in Rat Mandibular Bone Defects" Dental Materials Journal 2009 28(2):153-161.

Matsuno et al. "Development of β-tricalcium Phosphate/Collagen Sponge Composite for Bone Regeneration" Dental Materials Journal 2006 25(1):138-144.

* cited by examiner

BIODEGRADABLE COMPOSITE MATERIAL

This application is a U.S. national stage under 35 U.S.C. § 371 of PCT/EP2012/002309, filed May 31, 2012, which claims the benefit of priority from U.S. Provisional Application Ser. No. 61/491,480, filed May 31, 2011, and European Application No. 11 004 466.6, filed May 31, 2011, the contents of each of which are herein incorporated by reference in their entireties.

FIELD OF THE INVENTION

The invention relates to a biologically degradable composite material and to a process for the preparation thereof. The biologically degradable composite material according to the invention is preferably a bone reconstruction material which can be used in the field of regenerative medicine, especially as a temporary bone defect filler for bone regeneration.

PRIOR ART

Bone defects and the treatment thereof have been known for a long time. For example, bone defects can arise in the case of traumatic events (fractures). In addition, bone defects can also be brought about by diseases, for example tumours, osteolysis caused by osteoporosis or by absence of load, such as in the case of alveolar ridge atrophy. In all those cases, osseous defects are present which must be treated by regenerative measures.

The reservoir of endogenous (autogenous) bone suitable for transplantation is very limited: removal of bone for reconstruction at another site can be effected in the region of the iliac crest, in the chin or the angle of the jaw, at the head of the tibia or by removal at a rib or at the fibula. In addition to the limited availability, the removal of autogenous bone is associated with considerable risks for the patient, such as further surgery for bone removal and the possibility of consequent discomfort at the removal site.

In addition to the removal of autogenous bone, mention should be made of donor bones (allogenic bones, allografts) from human donors. Such bones are processed using laborious chemical methods in order to remove all allergenic foreign material from the bone. In addition to the risks of rejection reactions, mention should also be made of the difference in the bone mineral according to the age and lifestyle of the donors, which does not guarantee a reproducible therapeutic outcome even after an absolutely reproducible preparation process. This is described in the publication GRYNPAS, "Age and disease-related changes in the mineral phase of bone", Calcif. Tissue Int. 1993, 53 (1): 57-64.

As a further possible method of replacing autogenous bone, various attempts have been made to process mammalian bones in such a way that all the organic material is removed. In these cases too, there is still a residual risk of immune response and equally the possibility that diseases will cross the species barrier. Nowadays sophisticated technologies are used to minimise such risks in the case of so-called xenogenic bone replacement materials.

In addition to the risks mentioned, many materials of biological origin also have a problem in respect of X-ray opacity: the therapist may find it very difficult to distinguish the bone transplants from the healthy osseous environment in an X-ray image and accordingly may not always be able to check satisfactorily that defect filling has been successful and complete and to monitor the progress of healing. EP 0 932 373 therefore proposes a bone implant consisting of demineralised and partially demineralised bone particles which is provided with a radio-opaque marker.

The development of alternative biomaterials requires knowledge of the metabolism and of natural bone reconstruction and degradation processes. Bone is constantly being formed by osteoblasts and resorbed by osteoclasts. The degradation of a biomaterial takes place both by cellular absorption and by hydrolytic degradation.

Signal proteins, which are secreted by mammalian cells in order to influence neighbouring cells, were identified in the 1960s (Urist, Marshall R. (1965). "Bone: formation by auto-induction". *Science* 12:150 (698): 893-899). They act osteoinductively, that is to say they are able to induce bone growth. These so-called Bone Morphogenetic Proteins (BMPs) and various growth factors, such as Transforming Growth Factor Beta (TGF-β), Insulin-Like Growth Factor (IGF) and other cytokines result in highly accelerated bone growth. Efforts are being made to produce these proteins using recombinant biotechnology in order not to extract them from the bones or other body parts of mammals. In order to achieve retarded release of the materials, matrices are provided, on or in which the cytokines are immobilised. Such matrices can be, for example, bone reconstruction materials, bioceramics, organic polymers and also collagen or gelatin.

As a result of the above-mentioned multiplicity of problems associated with the use of autogenous bone, donor bone or xenogenic bone, research into alternatives in the form of synthetic biomaterials able to replace or supplement the use of natural bone materials was begun at an early stage.

In the case of synthetic biomaterials, a distinction is drawn between bone replacement and bone reconstruction materials. Bone replacement material is not absorbable or is only very slightly absorbable and, once healing is complete, forms a bone/bone replacement material construct in the defect. In contrast, bone reconstruction materials are fully absorbable and are replaced over the course of time by endogenous local bone. Synthetic bone replacement or bone reconstruction materials consist, for example, of calcium phosphates that have been sintered or precipitated from solution, for example hydroxyapatite (HA, $Ca_{10}(PO_4)_6(OH)_2$) or beta-tricalcium phosphate (β-TCP, $Ca_3(PO_4)_2$); bioceramics, such as bioglass or glass ceramics; or biologically degradable plastics. Typical bone replacement materials consist, for example, of HA or titanium. Typical bone reconstruction materials consist of β-TCP, bioglass, absorbable glass ceramics or biologically degradable plastics such as polyesters.

The regeneration potential of a bone reconstruction medium is to a substantial extent determined by the specific morphology of its porosity. Pores and cavities are important for penetration by blood and bodily fluids, for providing nutrients to the cells and for the break-up/degradation of the material. While an interconnecting micropore network primarily ensures the biocompatibility of the material, interconnecting macropores in a size range of from 100 to 500 μm primarily promote osseous growth through the material. Both in composite materials and in loose granules, the intergranular spaces should likewise be understood as being pores when their relation to bone ingrowth behaviour is being described.

Particle size and particle morphology are also essential to the regeneration potential of a bone reconstruction medium. Small particles lead to inflammatory, aseptic inflammation reactions. For example, it has long been known that abrasion, especially of the joint surfaces of artificial joints, leads to inflammatory reactions brought about by the phagocytic removal of particles by giant foreign-body-scavenging cells (macrophages). This process, known as phagocytosis, can be described in simple terms as incorporation of the particles by or into a macrophage and subsequent removal thereof. Macrophagocytosis is the subject of numeral investigations. GONZALEZ et al. (O. Gonzalez, R. L. Smith, S. B. Goodman, "Effect of size, concentration, surface area and volume of polymethylmethacrylate particles on human macrophages in vitro", *Journal of Biomedical Materials Research* 1996 (30), 463-473) report on phagocytable (0.325 µm and 5.5 µm) and non-phagocytable (200 µm) particles. PETERS et al., in connection with biomaterials composed of beta-tricalcium phosphate, write that the average particle size should be in the range of greater than or equal to 7-10 µm in order to avoid phagocytosis phenomena (F. Peters, D. Reif, "Functional Materials for Bone Regeneration from Beta-Tricalcium Phosphate", Mat.-wiss. u. Werkstoffiech. 2004, 35 (4), 203-207).

Further important properties of bone reconstruction media are, for example, biocompatibility, stability, especially mechanical strength, absorbability, total porosity, adaptability to the bone defect, and ease of handling for the attending physician.

Biocompatibility is a basic requirement for bone reconstruction media, because it deter-mines the compatibility of the synthetic material with human tissue. A large number of factors play a role in biocompatibility. For example, the nature of the surface of a bone reconstruction medium is just as important to biocompatibility as its overall design (for example particle size, particle morphology, total porosity, and the morphology of the inter- and intra-granular porosity, that is to say pore size distribution and interconnection of the pores within and between the individual granular particles of a bone reconstruction medium) and chemical composition. In order that the endogenous defence cells do not identify the materials as foreign bodies it is essential that the bone reconstruction medium match the bone tissue to be replaced in terms of physical and chemical characteristics. A bone reconstruction medium will, however, always behave like a foreign body, as it is after all not an endogenous component.

To increase the biocompatibility it has been proposed, for example, to add collagen to the synthetic biomaterials, because in that way it is possible to obtain a bone analogue, on the assumption that bone consists of about 30% collagen of type 1 and 70% calcium-deficient carbonate apatite. Collagen is biocompatible and forms a preferred matrix for the adhesion of bone-forming cells (osteoblasts). Collagen of type 1 is the most common modification and is generally used in the field of regenerative medicine and in tissue engineering. Collagen can be extracted from human or animal tissue, for example skin or tendons. Organo-inorganic composites composed of collagen and calcium phosphates can be obtained by in vitro mineralisation or by conventional mixing and freeze-drying processes.

For example, collagen in a composite with hydroxyapatite has been described (Rodrigues et al., Characterization of a bovine collagen-hydroxyapatite composite scaffold for bone tissue engineering, *Biomaterials* 24, 2003, 4987-4997). The surface of the composite has Arg-Gly-Asp (RGD) protein sequences, which has a positive effect on the interaction of the osteoblast-specific integrins with the substrate surface. Composite materials composed of collagen and hydroxyapatite as well as various preparation methods are also described in the publication Wahl and Czernuska (Collagen-Hydroxyapatite Composites for Hard Tissue Repair, *European Cells and Materials,* 11, 2006, 43-56).

To increase mechanical strength, EP 1 413 321 proposes the use of a glass ceramics, especially calcium alkali orthophosphate glass ceramics, for example having the chemical composition $Ca_2KNa(PO_4)_2$. The material can also be doped with silicate and, in addition to having increased mechanical stability, exhibits increased bioactivity and long absorption times.

Numerous further synthetic bone replacement or bone reconstruction materials that differ in their overall design and/or their chemical composition are known. For example, bone replacement or bone reconstruction materials are described in EP 0267624, DE 29922585, DE 3717818, WO 2004/112855, EP 1413323, EP 0941130, WO 2009/00445, US 2003/009235, EP 0164483, U.S. Pat. No. 4,795,467, EP 0243178, EP 0984745, DE 3414924, DE 4222763, DE 3784646, U.S. Pat. No. 5,071,436, EP 0309241, EP 0386253, EP 1891984, WO 98/22154, EP 1150726, EP 1270025, US 2005/0159820, U.S. Pat. No. 7,189,263, WO 02/22045, DE 102006026000, WO 03/022319, US 2008/0187571, WO 2006/031196, U.S. Pat. No. 7,544,212, WO 2005/051447, WO 2006/095154, US 2006/0172918, WO 03/071991, DE 102005034421, US 2002/0133238 and EP 0302847.

The use of biologically active compounds in synthetic biomaterials has also already been proposed. For example, bone replacement or bone reconstruction materials in conjunction with osteogenic proteins, growth factors, antibiotics and further biologically active compounds have been described, for example, in WO 89/09787, WO 89/09788, DE 69403439, WO 02/051449, WO 96/39202, EP 1372748 and EP 1719531.

Despite the large number of known and commercially available bone replacement and bone reconstruction materials, the treatment of osseous defects in the field of orthopaedic surgery and equally of defects in the oral or maxillofacial region remains a great challenge for the therapist. The reason for this is that, until now, there has been no material available that matches the physical and chemical characteristics of bone tissue in an optimum way and at the same time has the desired mechanical strength, absorbability, adaptability to the bone defect and ease of handling for the attending physician.

A disadvantage of the bone replacement and bone reconstruction materials known hitherto is that they are frequently optimised in only one of the desired properties. For example, the absorbability, adaptability to the bone defect and ease of handling for the attending physician in the case of bone replacement and bone reconstruction materials having good mechanical strength is generally limited.

A further problem of known bone replacement and bone reconstruction materials is their low X-ray opacity, with the result that the success of the treatment cannot be monitored.

The morphology of the pores and the particle size of the bone replacement and bone reconstruction materials known hitherto can also give rise to problems. For example, bone cannot fully grow through bone replacement and bone reconstruction materials having pores that are too long and winding. Excessively long interconnecting macroporous systems also harbour the risk of germs being able to lodge in the closed ends of the macroporous systems where they evade systemic treatment with antibiotics, as described, for example, by PALM (Palm, F. "Cerasorb M—a new synthetic pure-phase β-TCP ceramic in oral and maxillofacial surgery", *Implants* 2006, 3 (September)). Furthermore, bone replacement and bone reconstruction materials having particles that are too small or that disintegrate into small particles during absorption or as a result of abrasion can provoke inflammatory reactions. Since bone replacement and bone reconstruction materials, being non-endogenous tissue, always behave like a foreign body, the occurrence of inflammatory, aseptic inflammation reactions remains a common problem to be observed when bone replacement and bone reconstruction materials are used.

The aim of the present invention was the provision of a new biologically degradable composite material, especially a bone reconstruction material, having improved properties in comparison with the prior art, such as, for example, reduced occurrence of foreign body reactions through prevention of phagocytosis, higher X-ray opacity and better ease of handling and adaptability to the bone defect.

DESCRIPTION OF THE INVENTION

The invention relates to a biologically degradable composite material, especially a bone reconstruction material, having improved properties.

For that purpose, the present invention provides a biologically degradable composite material, characterised in that the composite material contains at least an inorganic component (a); an inorganic component (b); and at least one organic component (c); wherein the densities of the inorganic component (a) and of the inorganic component (b) are different.

In particular, a biologically degradable composite material for bone reconstruction or replacement having an open-porous base structure is provided, characterised in that the composite material contains at least an inorganic component (a); an inorganic component (b); and at least one organic component (c); wherein the inorganic component (a) is a granular material and each granule has an intragranular porosity of 30-40% by volume, based on the volume of the granule; the inorganic component (b) is a granular material and each granule has an intragranular porosity of 60-70% by volume, based on the volume of the granule; and the densities of the inorganic component (a) and the inorganic component (b) are different.

The term "biologically degradable" means that the composite material can be degraded by cellular absorption and/or hydrolytic degradation in a patient's body.

The term "inorganic component", as used herein, means a biocompatible inorganic material suitable as a bone replacement or bone reconstruction material. Such materials are known in the prior art and include, for example, bioceramics, especially calcium phosphate ceramics, bioglass containing $SiO_2$, $Na_2O$, $K_2O$, $CaO$ and/or $P_2O_5$, glass ceramics, or mixtures thereof.

The term "organic component", as used herein, means a biocompatible organic compound or a biocompatible organic material that can be used in bone replacement or bone reconstruction material. Such compounds or materials are known in the prior art and include, for example, biologically degradable plastics, such as polyester, polymers of lactic acid or glycolic acid, gelatin, collagen, glycosaminoglycan, hyaluronan, sodium hyaluronate, calcium hyaluronate, methyl cellulose, ethyl cellulose, propyl cellulose, hydroxypropyl cellulose, hydroxyethyl cellulose, starch, dextran, hydroxyethyl starch, alginate, polyethylene glycol, albumin, chitosan, polypeptides, proteins and antibiotics.

Preferably, the biologically degradable composite material is characterised in that the inorganic component (a) is present in an amount of 2-20% by weight, based on the composite material; the inorganic component (b) is present in an amount of 60-78% by weight, based on the composite material, and the organic component (c) is present in an amount of 10-20% by weight, based on the composite material, with the proviso that the total amount of the components contained in the composite material is not more than 100% by weight.

The biologically degradable composite material can also be characterised in that the density of the inorganic component (a) is approximately 0.8-1.5 $g/cm^3$ and the density of the inorganic component (b) is approximately 0.5-0.9 $g/cm^3$, with the proviso that the density of the inorganic component (b) is less than that of the inorganic component (a) and the difference in density is at least 0.1 $g/cm^3$.

The biologically degradable composite material can also be characterised in that the bulk density of the inorganic component (a) is approximately 0.8-1.5 $g/cm^3$ and the bulk density of the inorganic component (b) is approximately 0.5-0.9 $g/cm^3$, with the proviso that the bulk density of the inorganic component (b) is less than that of the inorganic component (a) and the difference in density is at least 0.1 $g/cm^3$.

The difference in density is the difference between the densities of the inorganic component (a) and the inorganic component (b) (difference in density=[density of the inorganic component (a)]−[density of the inorganic component (b)]).

The biologically degradable composite material can additionally contain an inorganic component (d). Preferably, such a composite material is characterised in that the inorganic component (a) is present in an amount of 2-20% by weight, based on the composite material; the inorganic component (b) is present in an amount of 60-78% by weight, based on the composite material; the inorganic component (d) is present in an amount of 0.1-28% by weight, based on the composite material; and the organic component (c) is present in an amount of 10-20% by weight, based on the composite material, with the proviso that the total amount of the components contained in the composite material is not more than 100% by weight. Preferably, the biologically degradable composite material can be characterised in that the inorganic component (a) and/or the inorganic component (b) and/or, if present, the inorganic component (d) contain(s) micropores and/or mesopores and/or macropores. According to the invention, pores <10 μm are micropores, pores of 10-50 μm are mesopores and pores >50 μm are macropores. Preferably, the micropores, mesopores and/or macropores can interconnect. More preferably, the micropores form an interconnecting network into which discrete mesopores and macropores have been introduced in homogeneous distribution.

More preferably, the biologically degradable composite material can be characterised in that the porosity of the inorganic component (a), of the inorganic component (b) and/or, if present, of the inorganic component (d) is 20-85% by volume, in each case based on the total volume of the inorganic component.

Preferably, the biologically degradable composite material can further be characterised in that the inorganic component (a), the inorganic component (b) and, if present, the inorganic component (d) is a granular material containing biologically active, polygonal, rounded particles which consist of calcium phosphate and/or sodium-containing and/or potassium-containing and/or calcium-containing and/or silicate-containing acidic and/or neutral and/or alkaline bioglass, glass ceramics or mixtures thereof.

Preferably, the biologically degradable composite material can also be characterised in that the inorganic component (a) and/or the inorganic component (b) and/or, if present, the inorganic component (d) is a granular material containing biologically active, polygonal, rounded particles which consist of calcium phosphate having from 0 to 25% by weight of a silicate glass additive, based on the calcium phosphate, without there being any change in the crystalline structure of the calcium phosphate crystal lattice, the calcium phosphate being selected from beta-tricalcium phosphate, preferably pure-phase β-tricalcium phosphate having from 0 to 15% by weight of a sodium magnesium silicate glass additive, monocalcium phosphate monohydrate, anhydrous monocalcium phosphate, dicalcium phosphate dihydrate, anhydrous dicalcium phosphate, β-tricalcium phosphate, tetracalcium phosphate, whitlockite, octacalcium phosphate, hydroxyapatite, oxyapatite, carbonate apatite of type A, carbonate apatite of type B, calcium-deficient hydroxyapatite, amorphous calcium phosphate, amorphous carbonate-containing calcium phosphate, calcium alkali orthophosphate glass ceramics, or mixtures thereof.

Furthermore, the biologically degradable composite material can preferably be characterised in that the inorganic component (a) is a granular material having particles of a size of 1000-2000 μm, the inorganic component (b) is a granular material having particles of a size of 150-500 μm, and, if present, the inorganic component (d) is a granular material having particles of a size of 150-500 μm and a total porosity of approximately 50-60% by volume, based on the porosity of the inorganic component (a) or (b).

The total porosity denotes the sum of all pores present. The porosity is divided into intragranular porosity (that is to say the pores contained in a single granule of one of the inorganic components (a), (b) or (d)) and the intergranular porosity (that is to say the pores formed by the interstices between the granules of the inorganic component in question). The total porosity is determined on the basis of the bulk and tamped densities of the granules of the inorganic component in question. The bulk density (weight/volume) of the inorganic component in question is determined by filling a measuring cylinder with the inorganic component up to a fixed volume (volume) and determining the weight of the inorganic component by weighing. The material is then tamped by means of 500 strokes of a tamping volumeter and the volume in the measuring cylinder is measured again; the density ascertained (weight/volume) gives the tamped density. Tamping volumeters are commercially available, for example tamping volumeter SVM22 from Erweka. The determination of the tamped volume is carried out in accordance with the European Pharmacopoeia, Ph. Eur 4, 2002; Chapter 2.9.15 Bulk and tamped densities.

Preferably, the biologically degradable composite material can be characterised in that the inorganic component (a) is a granular material having particles of a size of 150-500 μm and a density of 0.9-1.5 g/cm$^3$, and the inorganic component (b) is a granular material having particles of a size of 1000-2000 μm and a density of 0.6-0.8 g/cm$^3$.

Granular inorganic biomaterials are usually available in various particle size ranges. Particles of a specific particle size (granule diameter) are obtainable, for example, by comminution of relatively large broken fragments of bioceramics and subsequent separation by sieving using a sieve cascade. For sieving, commercial sieving machines, for example the Fritsch Analysette 3 vibrating sieving machine, are available. Granular materials having particles of a specific size (particle size) can be obtained by using suitable test sieves (according to DIN4197) of defined mesh sizes (mean value), for example 0.15 mm, 0.25 mm, 0.5 mm, 1 mm, 2 mm, 4 mm. For example, particles of 150-500 μm can be obtained by first sieving the bioceramics with a test sieve of mesh size 0.5 mm (500 μm) and then sieving the material that has passed through the sieve (particles 500 μm) with a test sieve of mesh size 0.15 mm (150 μm), the retained material (residue on the sieve) being particles having a size of 150-500 μm, while the particles that have passed through the sieve have a size of ≤150 μm. After sieving, the individual fractions are weighed and their distribution thus determined.

Preferably, the inorganic component (a) has an intragranular porosity (that is to say the sum of all micropores, mesopores and/or macropores contained in a single granule (particle)) of 30-40% by volume, preferably 35% by volume, based on the volume of a single particle of the inorganic component.

Preferably, the inorganic component (b) has an intragranular porosity of 60-70% by volume, preferably 60% by volume, based on the volume of a single particle of the inorganic component.

Preferably, the biologically degradable composite material can be characterised in that the inorganic component (a), (b) and, if present, (d) is a granular material the primary particles of which have a d50 value of at least 10 μm. The d50 value is determined by laser light scattering. For that purpose corresponding products are commercially available, for example the Fritsch Analysette 22 laser particle sizer having a NeNe laser (wavelength 632.8 nm, laser output 4 mW, laser class IIIB); the particle size distribution is calculated in accordance with the Fraunhofer or Mie theory.

"Primary particles" are understood to be the starting particles of the inorganic component which are aggregated by sintering to form granules; the granules are an agglomerate of the primary particles in which the primary particles are firmly bonded to one another.

The particle size of a granule (a particle of the granular material) of the inorganic component (a), of the inorganic component (b) and of the inorganic component (d) can be 150-4000 μm. Preferably, the granular material of the inorganic components (a), (b) and, if present, (d) can be composed of sintered primary particles that are <63 μm. According to the invention, the use of primary particles of <63 μm and a d50 value of at least 10 μm is preferred.

Preferably, the biologically degradable composite material can be characterised in that the inorganic components (a), (b) and, if present, (d) are in each case a granular material composed of pure-phase beta-tricalcium phosphate having from 0 to 15% by weight of a sodium magnesium silicate glass additive, based on the beta-tricalcium phosphate, or from 0 to 100% by weight of a calcium alkali orthophosphate glass ceramics additive, especially $Ca_2KNa(PO_4)_2$, based on the beta-tricalcium phosphate.

Especially preferably, the biologically degradable composite material can be characterised in that the inorganic components (a), (b) and, if present, (d) are in each case a granular material composed of pure-phase beta-tricalcium phosphate having from 0 to 15% by weight of a sodium magnesium silicate glass additive, based on the beta-tricalcium phosphate, or a granular material composed of calcium alkali orthophosphate glass ceramics, having from 1 to 15% by weight of a sodium magnesium silicate glass additive (based on the calcium alkali orthophosphate glass ceramics), especially Si-doped $Ca_2KNa(PO_4)_2$.

A granular material composed of pure-phase beta-tricalcium phosphate having from 0 to 15% by weight of a sodium magnesium silicate glass additive, based on the beta-tricalcium phosphate, can be prepared as described below for constituent M.

A granular material composed of calcium alkali orthophosphate glass ceramics having from 1 to 15% by weight, preferably from 1 to 5% by weight, of a sodium magnesium silicate glass additive (based on the calcium alkali orthophosphate glass ceramics) can be prepared as described below for constituent N.

Furthermore, the biologically degradable composite material can be characterised in that the at least one organic component (c) is selected from gelatin, collagen, glycosaminoglycan, hyaluronan, sodium hyaluronate, calcium hyaluronate, methyl cellulose, ethyl cellulose, propyl cellulose, hydroxypropyl cellulose, hydroxyethyl cellulose, starch, dextran, hydroxyethyl starch, alginate, polyethylene glycol, albumin, chitosan, organically processed or demineralised allogenic or xenogenic bone, synthetic polypeptide, parathormone, osteogenic protein, or a combination thereof.

Preferably, the biologically degradable composite material can be characterised in that the collagen of the at least one organic component (c) is a native and/or renatured collagen.

Furthermore, the biologically degradable composite material can preferably be characterised in that the collagen of the at least one organic component (c) is of animal origin, preferably of porcine or bovine origin.

Preferably, the biologically degradable composite material can be characterised in that the collagen of the at least one organic component (c) is a collagen of type I, II or III, or a combination thereof.

Furthermore, the biologically degradable composite material can be characterised in that the osteogenic protein of the at least one organic component (c) is selected from OP-1, OP-2, OP-3, BMP2, BMP3, BMP4, BMP5, BMP6, BMP9, BMP10, BMP11, BMP12, BMP14, BMP15, BMP16, IGF, TGF, PDGF, GDF1, GDF3, GDF5, GDF6, GDF7, GDF8, GDF9, GDF10, GDF11, or a combination thereof.

Preferably, the biologically degradable composite material can be characterised in that the at least one organic component (c) encapsulates the inorganic components (a), (b) and, if present, (d) and/or is contained in, and plugs, the pores of the inorganic components (a), (b) and, if present, (d).

Furthermore, the biologically degradable composite material can be characterised in that the at least one organic component (c) and the inorganic components (a), (b) and, if present, (d) are cross-linked.

The biologically degradable composite material can also be characterised in that it contains as additives further components, comprising (i) an aqueous solution of a hydrogel-forming substance, the hydrogel-forming substance being selected from modified cellulose, starch, methyl cellulose, carboxymethyl cellulose, hydroxymethyl cellulose, dextran, hyaluronic acid, sodium hyaluronate, polyethylene glycol, or a combination thereof; and/or (ii) at least one anti-bacterial, wound-healing-promoting, bone-growth-promoting and/or coagulation-inhibiting substance, in the pores and/or on the surface of the composite material.

Preferably, the biologically degradable composite material can be characterised in that the density of the composite material is from 0.1 to 2 g/cm$^3$, preferably from 0.2 to 0.4 g/cm$^3$. The "density of the composite material" denotes the bulk density (weight/volume), which is determined by filling a measuring cylinder with the composite material up to a fixed volume and ascertaining the weight of the composite material by weighing.

Preferably, the biologically degradable composite material can be characterised in that the specific surface area of the composite material is from 0.1 to 2 m$^2$/g, preferably from 0.2 to 0.4 m$^2$/g. The specific surface area is determined using the gas adsorption method in accordance with Brunauer Emmett and Teller (BET).

Preferably, the biologically degradable composite material can be characterised in that the ratio between the density and the specific surface area of the composite material is from 0.1 to 3, preferably from 0.5 to 0.7 or from 1.5 to 2.0.

The biologically degradable composite material can preferably also be characterised in that according to combustion analysis of the composite material the ratio between the density and the volume shrinkage is from 0.1 to 1.0, preferably from 0.2 to 0.3 or from 0.5 to 0.7. For the combustion analysis, the composite material is "burnt" in air for >30 min (up to two hours) at 800° C. The volume shrinkage is ascertained by determining the volume of the sample by means of water displacement before and after combustion. The difference in the volume before the combustion analysis and the volume after the combustion analysis is used to ascertain the volume shrinkage.

The biologically degradable composite material can be present in a geometric standard shape, preferably in the shape of a rectangle, parallelepiped, cylinder or cube, or in the shape of the bone defect, preferably in the hollow spherical shape of an acetabulum or in the conical shape of an extraction alveolus.

Preferably, the biologically degradable composite material can be in sterile form.

According to the invention, the biologically degradable composite material also includes all combinations of the features mentioned above, special preference being given to combinations of preferred features.

The invention relates also to a process for preparing a composite material according to the invention, comprising the following steps:

(S1) adding the at least one organic component (c) to a water-containing solution to form a suspension;

(S2) adding the inorganic components (a), (b) and, if present, (d); and, optionally, a cross-linking agent; to the suspension from step (S1) and mixing the components to form a solution;

(S3) transferring the solution from step (S2) to a mould and then drying the mixture by lyophilisation to form the composite material.

Preferably, the process according to the invention can be characterised in that in step (S3) after the lyophilisation the composite material is additionally subjected to a heat treatment at from 80 to 120° C. for from 0.25 to 48 hours.

Furthermore, the process according to the invention can be characterised in that, as cross-linking agent, an organic acid or an aqueous or alcoholic solution of an organic acid is added to the suspension from step (S1), preferably formic acid, acetic acid, propionic acid, or an aqueous or alcoholic solution of methanoic acid (formic acid), ethanoic acid (acetic acid), propanoic acid (propionic acid), butanoic acid (butyric acid), n-butyric acid, isobutyric acid, pentanoic acid (valeric acid), n-valeric acid, isovaleric acid, 2-methylbutyric acid, pivalic acid, oxalic acid, malonic acid, succinic acid, glutaric acid, adipic acid, pimelic acid, hydroxyacetic acid (glycolic acid), hydroxypropionic acid (lactic acid), D-lactic acid, L-lactic acid and racemates thereof, beta-hydroxypropionic acid, alpha-hydroxyvaleric acid, beta-hydroxyvaleric acid, gamma-hydroxyvaleric acid, hydroxymalonic acid (tartronic acid), D-hydroxysuccinic acid (malic acid), L-hydroxysuccinic acid and racemates thereof, dihydroxysuccinic acid (tartaric acid) enantiomerically pure and racemates thereof (racemic acid), propenoic acid (acrylic acid), fumaric acid, maleic acid, citric acid, mesoxalic acid, acetonedicarboxylic acid, oxalacetic acid, aconitic acid, tricarballylic acid, ascorbic acid, formaldehyde, glutaraldehyde, genipin, glucose, fructose, maltose, dextrose, saccharose, or combinations thereof.

Preferably, the process according to the invention can be characterised in that the solution in step (S2) is foamed by the introduction of gas or by mechanical manipulation and step (3) is carried out with a foamed solution, the shaping of the composite material being carried out before or after the lyophilisation or the heat treatment.

Unless otherwise indicated, all amounts and percentages by weight (% by weight) contained herein relate to the total weight of the composite material.

A biologically degradable composite material according to the invention for bone reconstruction or replacement having an open-porous base structure, can be prepared by
(i) adding at least one organic component (c) to a water-containing solution to form a suspension;
(ii) adding to the suspension from (i), as inorganic component (a), a granular material having particles of a size of 1000-2000 µm and a bulk density of 0.8-1.5 g/cm$^3$, as inorganic component (b) a granular material having particles of a size of 150-500 µm and a bulk density of 0.8-1.5 g/cm$^3$, as inorganic component (d) a granular material having particles of a size of 150-500 µm and a bulk density of 0.8-1.5 g/cm$^3$, and, optionally, a cross-linking agent and mixing the components to form a solution;
(iii) transferring the solution from (ii) to a mould and then drying the mixture by lyophilisation to form the composite material.

Preferably, in step (ii) acetic acid is used as cross-linking agent.

As inorganic component (a), (b) and (d), pure-phase beta-tricalcium phosphate is especially suitable.

As organic component (c), porcine collagen, preferably porcine collagen of type I or type 3, or a mixture thereof, is especially suitable.

Furthermore, a biologically degradable composite material according to the invention for bone reconstruction or replacement having an open-porous base structure, can be prepared by
(i) adding porcine collagen to a water-containing solution to form a suspension;
(ii) adding to the suspension from (i), as inorganic component (a), a granular material composed of pure-phase beta-tricalcium phosphate having from 2 to 10% by weight of a sodium magnesium silicate glass additive, based on the beta-tricalcium phosphate, having particles of a size of 1000-2000 µm, as inorganic component (b) a granular material composed of pure-phase beta-tricalcium phosphate having from 2 to 10% by weight of a sodium magnesium silicate glass additive, based on the beta-tricalcium phosphate, having particles of a size of 150-500 µm, and acetic acid as cross-linking agent and mixing the components to form a solution;
(iii) transferring the solution from (ii) to a mould and then drying the mixture by lyophilisation to form the composite material.

Furthermore, a biologically degradable composite material according to the invention for bone reconstruction or replacement having an open-porous base structure, can be prepared by
(i) adding porcine collagen to a water-containing solution to form a suspension;
(ii) adding to the suspension from (i), as inorganic component (a), a granular material composed of a calcium alkali orthophosphate glass ceramics additive, doped with from 1 to 5% by weight silicon (based on the calcium alkali orthophosphate glass ceramics additive), having particles of a size of 1000-2000 µm, as inorganic component (b) a granular material composed of a calcium alkali orthophosphate glass ceramics additive, doped with from 1 to 5% by weight silicon (based on the calcium alkali orthophosphate glass ceramics additive), having particles of a size of 150-500 µm, and acetic acid as cross-linking agent and mixing the components to form a solution;
(iii) transferring the solution from (ii) to a mould and then drying the mixture by lyophilisation to form the composite material.

An advantage of the novel biologically degradable composite material is that there is thus provided a flexible material for bone reconstruction or bone replacement which in its embodiments can be modelled, kneaded or returned to its original shape. The composite material according to the invention therefore exhibits extraordinary ease of handling and can be tailored to the bone defects in question. The composite material according to the invention is biocompatible and osteoconductive, that is to say it forms a guideway for newly formed bone. Furthermore, all the components of the composite material according to the invention can be absorbed by the organism, that is to say can undergo cellular or hydrolytic degradation.

A particular advantage is that the healing process can be monitored radiologically, because the composite material according to the invention can be distinguished from the biological environment at the site of implantation on account of its higher X-ray opacity.

A further advantage of the composite material according to the invention lies in the difference in the residence times of the components used, the residence time being the length of time a material remains in the organism before it is 100% absorbed. The residence time of the at least one organic component (c) is shorter than that of the inorganic components (a), (b) and, where applicable, (d). Ideally, the inorganic component is fully replaced by bone, which grows relatively slowly, within a period of from 3 to 6 months, whereas the organic component has a residence time of only 3-8 weeks. By virtue of the preparation technique, the organic component can, for example, be cross-linked, which makes it possible to adjust the residence times of the organic component of 3 to 8 weeks in a controllable way. The inhibiting effect of the organic component ensures that recrystallisation of the inorganic component, for example calcium phosphate phase transition, does not take place.

Furthermore, the composite material according to the invention is not limited to application using a specific means of application; it is suitable for universal use, that is to say with all means of application customary in the field of medicine, especially in the field of dental medicine and the field of plastic surgery, such as, for example, a spatula, scalpel, tweezers, brush, knife or an injection or cartridge system. It is also possible for the composite material according to the invention to be cut without disintegrating into small particles.

The composite material according to the invention has an open-porous base structure which both has haemostatic (haemostyptic) properties and allows the composite material according to the invention to acquire blood vessels (angiogenesis) and tissue: blood vessels and connective tissue grow into the composite material according to the invention in the early phase of bone healing. The blood vessels enable the cells and the incipient tissue compartments to be supplied with oxygen and nutrients inside the composite material according to the invention. By the time a sufficiently dimensionally stable connective tissue structure is present, the organic component has been fully absorbed. The composite material according to the invention is replaced by endogenous local bone, which encourages bone growth and, as a result of its place-holder function, prevents the ingrowth of faster-growing connective tissue.

A further advantage of the composite material according to the invention is its mechanically very stable structure. This structure enables the porosity of the composite material according to the invention to be increased and its bioactivity enhanced. Furthermore, the structure of the composite material according to the invention is stabilised in such a way that the material is attacked or decomposes only after prolonged treatment with organic acid. The action of acid over the period of from 0 to 6 hours in accordance with the invention affects neither the phase stability nor the primary particle size. Only after being acted upon for a period of 6 hours is there any identifiable reduction in the size of the primary particles, which still does not fall below the critical threshold for initiating phagocytosis.

A special advantage of the composite material according to the invention is that wound-healing problems are relatively rare. For example, the pores of the composite material according to the invention are preferably plugged at the time of implantation in order that initially the material cannot be penetrated by pathogens that evade systemic treatment with antibiotics. If the pores are filled with collagen, as is preferred, it is also possible for an antibiotic to move through the open sponge-like collagen structure. Furthermore, in the acute phase of wound healing after implantation, increased macrophagocytic activity is always observed. As a consequence of such acute inflammatory reactions, it is possible for soluble inorganic bioceramics to be attacked, leading to disintegration into small sub-particles. These small sub-particles can in turn trigger further phagocytic reactions and accordingly significantly increase the risk of an aseptic foreign body reaction. Because the composite material according to the invention has a mechanically very stable structure, such processes are avoided. An additional safeguard against premature particle disintegration during the initial period after implantation is provided by the preferred, full encapsulation of the inorganic components by the organic component. The surface structure of the composite material according to the invention is uniform and therefore particularly biocompatible, especially if the organic component fully encapsulates the inorganic components.

Figure 1:
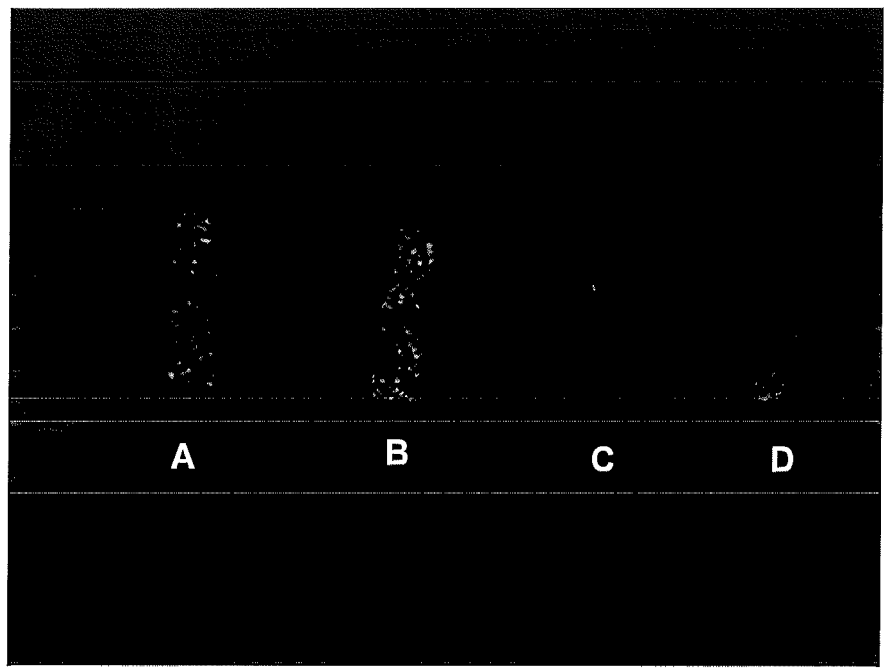
FIG. 1: Comparative X-ray images of composite material according to the invention with commercially available bone replacement material. A: collagen/TCP composite according to the invention having a density of 0.2 g/cm$^3$, B: collagen/TCP composite according to the invention having a density of 0.4 g/cnn$^3$, C: VITOSS Foam Pack low density, D: VITOSS Foam Strip high density. The nature of the composite material according to the invention is more uniform and therefore more biocompatible than in the case of the commercial product. Furthermore, the granular particles are far more prominent by virtue of their differences in density, with the result that the X-ray opacity is higher and the material can be seen more easily in the osseous environment in an X-ray image.
Figure 2:
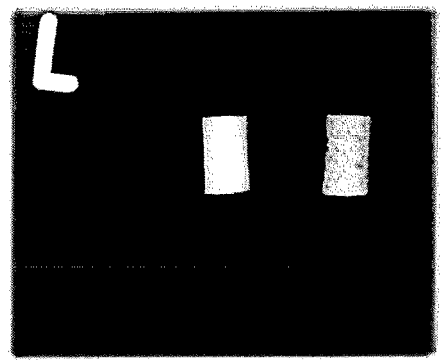
FIG. 2: X-ray image in transmission of two gelatin/ceramics composite materials according to the invention showing A: particle sizes of the ceramics 150-500 µm and B: 500-1000 µm. The high degree of X-ray opacity and the uniform surface structure can be seen.

The invention will be explained below on the basis of Examples.

EXAMPLES

For the preparation of the composite materials according to the invention, constituents A, B, C, D, E, F, G, H, I, K, L, M, N, O, P, Q and R are provided. The constituents are as follows:

Constituent A: 99% pure-phase β-tricalcium phosphate, particulate, a bulk density of 1.1±0.1 g/cm$^3$ and a particle size of <63 µm ($d_{50}$=15±5 µm).

Constituent B: bioabsorbable sintered glass consisting of 75±5% by weight $SiO_2$, 9±3% by weight MgO and 15±5% by weight $Na_2O$. Such glass is described in the patents having the application numbers EP 03 090 348 and EP 03 090 349.

Constituent C: Rapidly absorbable glass ceramics of the chemical formula $Ca_2KNa(PO_4)_3$ having the following element composition: 23±2% by weight Ca, 11.5±2% by weight K, 6.5±2% by weight Na, 55±2% by weight $PO_4$, 2.5±1% by weight Mg. Glass ceramics of this kind is described in the patents having the application numbers EP 03 090 348 and EP 03 090 349.

Constituent D: Water for injection purposes.

Constituent E: Ammonium hydrogen carbonate having a particle size of <10 µm.

Constituent F: Ammonium hydrogen carbonate having a particle size of 10-50 µm.

Constituent G: Ammonium hydrogen carbonate having a particle size of 50-500 µm.

Constituent H: Constituent A is sprayed intermittently with constituent D on a pan granulator performing rolling movements, so that rolling-up occurs in accordance with the snowball effect. After a 5-hour sintering operation at 1000° C. and subsequent sieving, spherical granules have formed in fractions of 150-5000 µm having a porosity of approximately 30-40% and a density of about 1.2 g/cm$^3$. X-ray powder diffractometry confirms pure-phase β-tricalcium phosphate. The specific surface area, measured by the BET method with krypton as measuring gas, gave values in the range of 0.1-0.15 m$^2$/g.

Constituent I: Constituent A is intimately mixed with 10% by weight constituent E, 20% by weight constituent F and 10% by weight constituent G and subjected to cold isostatic pressing. A sublimation process at 80° C. for 12 hours and a subsequent sintering operation at 1000° C. for 5 hours are followed by comminution and sieving. A subsequent sintering operation at 1000° C. for 5 hours yields granules of the size 150-8000 µm, which have a porosity of about 65% and a bulk density of 0.8 g/cm$^3$ and are pure-phase according to X-ray powder diffractometry. The pore distribution is discrete, that is to say only the micropores, i.e. pores <10 µm, are interconnected with one another. Mesopores (10-50 µm) and macropores (>50 µm) are discretely distributed in the interconnecting microporous network and, through the micropores, are accessible to blood and bodily fluids. X-ray powder diffractometry confirms pure-phase β-tricalcium phosphate. Measurements using the BET method with krypton as measuring gas revealed a specific surface area of 0.15-0.2 m²/g.

Constituent K: Reticulated polyurethane sponges, produced in accordance with the Schwartzwalder-Somers method with a pore size distribution of 45 pores per inch (ppi, corresponds to a pore size of 1000 µm).

Constituent L: Reticulated polyurethane sponges, produced in accordance with the Schwartzwalder-Somers method with a pore size distribution of 80 pores per inch (ppi, corresponds to a pore size of 500 µm).

Constituent M: Constituent A is made into a slurry with constituent D; 5% by weight constituent B are added and the mixture is finely ground so that a thixotropic slurry having a particle size distribution of 2-5 µm ($d_{50}$) is obtained. Half of the slurry is kneaded into constituent K and half into constituent L. After sintering at 1000° C. for 5 hours, the PU foam has been totally burnt-out without residue, leaving behind a closely sintered ceramics having pore sizes of 400 µm (starting constituent K) and 250 µm (starting constituent L). Comminution, sieving and further sintering under the same conditions yield granules of particle sizes 150-8000 µm having a total porosity of 80% and a bulk density of approximately 0.6 g/cm³, in each case having the pore diameters mentioned for the respective half. X-ray powder diffractometry confirms pure-phase β-tricalcium phosphate.

Constituent N: Constituent C is made into a slurry with constituent D; 5% by weight constituent B are added and the mixture is finely ground so that a thixotropic slurry having a particle size distribution of 2-5 µm ($d_{50}$) is obtained. Half of the slurry is kneaded into constituent K and half into constituent L. After sintering at 1000° C. for 5 hours, the PU foam has been totally burnt-out without residue, leaving behind a closely sintered ceramics having pore sizes of 400 µm (starting constituent K) and 250 µm (starting constituent L). Comminution, sieving and further sintering under the same conditions yield granules of particle sizes 150-8000 µm having a total porosity of 80% and a bulk density of approximately 0.6 g/cm³, in each case having the pore diameters mentioned for the respective half. X-ray powder diffractometry confirms correspondence to the phase $KNaCa_2(PO_4)_2$ (PDF #51-579).

Constituent O: Porcine collagen, mainly of type 1, obtained from the tissue of pigs that have been raised under controlled conditions. The material has been declared "fit for human consumption". The porcine tissue is processed under controlled environmental conditions. The collagen is highly purified. Only trace residues of the preparation process are present and toxic effects are therefore excluded.

Constituent P: Acetic acid 100%

Constituent Q: Porcine gelatin obtained from the tissue of pigs that have been raised under controlled conditions. The material has been declared "fit for human consumption". The porcine tissue is processed under controlled environmental conditions.

Constituent R: Genipin

Example 1

The particle fraction 1000-2000 µm of constituent I is separated out by sieving and 5.6 g portions thereof were each suspended in 20 ml of constituent D, and 74 µl of constituent P are added thereto. After 0, 1, 3, 6 and 23 hours, the material was filtered, washed and dried. The particles were then washed, filtered off and dried and tested for particle size using a laser scattering apparatus (Fritsch Analysette), tested for the integrity of the surface by means of scanning electron microscopy and tested for phase purity by means of X-ray powder diffractometry. Table 1 shows $d_{10}$, $d_{50}$ and $d_{90}$ values of tricalcium phosphate powder after different periods under the action of acetic acid.

TABLE 1

| Hours in acetic acid | d10 | d50 | d90 |
| --- | --- | --- | --- |
| 0 | 12.6 | 30.09 | 51.74 |
| 1 | 11.76 | 30.65 | 50.05 |
| 3 | 10.52 | 25.16 | 43.38 |
| 6 | 8.74 | 24.06 | 42.31 |
| 23 | 9.79 | 21.98 | 37.27 |

As can be seen from Table 1, only after 6 hours is there any appreciable reduction in particle sizes, the fines fraction, which is represented by the d10 value, being subject to greater degradation than the particulate disintegration of the coarser fractions. Accordingly, the surface etching of the small particles having relatively large surface areas is to be regarded as a greater influence than the particle boundary etching. Even after 23 hours, the fines fraction has not dropped substantially below the critical threshold of the phagocytable range, so that it is possible to rule out an increased risk of excessive foreign body reactions caused by the implantation of the constituent I in bones or tissue even after prolonged acid treatment.

Figure 3:
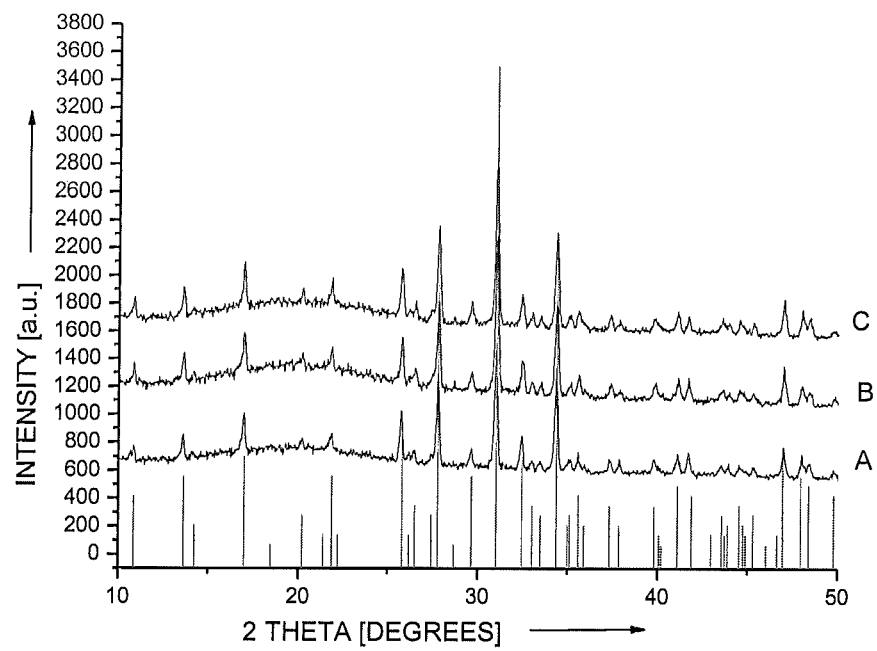
FIG. 3: X-ray powder diffractograms of collagen/TCP composites according to the invention before and after treatment with acetic acid. The PDF file #55-898 shows, in the form of a bar chart, pure-phase β-tricalcium phosphate as reference. The amorphous halo is caused by the reflection of the collagen. It can be seen that the phase purity of the calcium phosphate is not affected by the action of acetic acid.

The results of X-ray powder diffractometry in respect of phase purity are shown in FIG. 3. As can be seen from FIG. 3, the action of acetic acid also has no effect on the phase purity, so that it is possible to rule out both an increased risk of excessive foreign body reactions caused by the implantation of the constituent I in bones or tissue and a reduction in absorbability caused by transformation into a non-absorbable calcium phosphate phase after prolonged acid treatment.

Example 2

16.5 g of constituent O are added to 3.5 ml of constituent D and suspended by means of a colloid mill. The particle fraction 1000-2000 µm of constituent I is separated out by sieving and 5.6 g were added to the suspension. After addition of 74 µl of constituent P, the material is stirred at room temperature. After 0, 30, 120 and 165 minutes, the acid is neutralised and the mixture is poured into a mould and freeze-dried. X-ray powder diffractometry is used to test whether the action time of the acid has affected the phase stability of the calcium phosphate. The results show that the action of the acid has had no effect on the phase stability of the material.

Example 3

The granular fraction 150-500 µm is separated out from constituent H by sieving. The fractions 150-500 µm and 1000-2000 µm are separated out from constituent I by sieving. These components are mixed together in various ratios in accordance with Table 2.190 g of constituent O are suspended in 1000 ml of constituent D and ground by means of a colloid mill. 760 g of the granular mixture are added and the mixture is intimately mixed. After addition of 10 ml of constituent B, the mixture is neutralised, poured into a square high-grade steel mould and lyophilised. Depending upon the lyophilisation procedure (slow or fast) it is possible to obtain composite materials having densities of 0.2 or 0.4 g/ml. Table 2 provides information about the different mixtures and the densities and specific surface areas measured.

TABLE 2

Measurement results of various collagen/ceramics composites in comparison with collagen

| Sample | Constituent H 150-500 μm [% by mass] | Constituent I 150-500 μm [% by mass] | Constituent I 1000-2000 μm [% by mass] | Collagen [% by mass] | Density [g/ml] | Specific surface area [m²/g] | Ratio of density to surface area |
|---|---|---|---|---|---|---|---|
| CF-33 | 4 | 4 | 72 | 20 | 0.4 | 0.2605 | 1.54 |
| CF-34 | 2 | 6 | 72 | 20 | 0.4 | 0.25 | 1.6 |
| CF-35 | 4 | 12 | 64 | 20 | 0.4 | 0.2199 | 1.82 |
| CF-36 | 0 | 20 | 60 | 20 | 0.4 | 0.2152 | 1.86 |
| CF-37 | 4 | 4 | 72 | 20 | 0.2 | 0.3658 | 0.32 |
| CF-38 | 2 | 6 | 72 | 20 | 0.2 | 0.3092 | 0.65 |
| CF-39 | 4 | 12 | 64 | 20 | 0.2 | 0.306 | 0.66 |
| CF-40 | 0 | 20 | 60 | 20 | 0.2 | 0.3547 | 0.56 |
| Collagen | 0 | 0 | 0 | 100 | 0.3 | 1.5768 | 0.19 |

Figure 4:
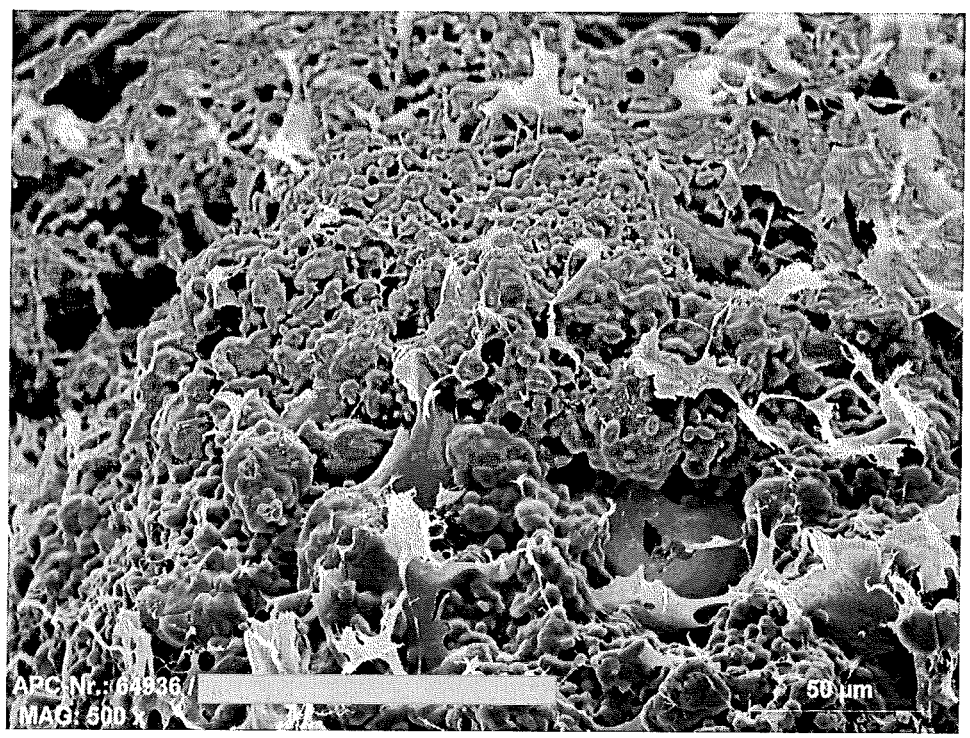
FIG. 4: shows a scanning electron microscope image of the ceramic surface of an embodiment of the composite material according to the invention having collagen as organic component. It will be seen that the porous structure of the ceramics is covered by the collagen; the collagen plugs the pores and the collagen fibres cross-link the granules of the inorganic components.

It will be seen that 100% pure collagen has a 5 to 8 times greater surface area. The porosity is therefore lastingly reduced. The pores of the ceramics are not accessible initially because the collagen has penetrated into the ceramics and permeated the porous ceramics structure (see, for example, FIG. 4). By adding the particulate calcium phosphates it is possible to adjust the ratio between density and specific surface area over a wide range.

Example 4

To determine the volume shrinkage and to monitor homogeneity, the composite materials according to the invention according to Example 3 were subjected to incineration analysis with density determination, wherein shaped bodies were cut out of the composites, the volume and weight thereof were determined and the density ascertained therefrom. The shaped bodies were then transferred to a crucible and the organic phase of the moulded bodies was incinerated in an oven without residue, leaving behind the ceramics, the weight and bulk density of which were determined after cooling. On the basis of this analysis it is possible to determine the percentages by volume of the organic and inorganic components and the volume that remains after the relatively rapid absorption. The results of the tests are compiled in Table 3. For comparison with the composite materials according to the invention, the two commercially available collagen/TCP composites "Vitoss Foam Strip" and "Vitoss Foam Pack" were also tested.

The volume shrinkage of composite materials according to the invention having a density of 0.2 g/cm³ is 70-80% once the collagens have been burnt out. The volume shrinkage of composite materials according to the invention having a density of 0.4 g/cm³ is 60-70% after burn-out. In respect of the ratio between density and shrinkage, the values for the composite materials according to the invention are therefore from 0.2 to 0.6. In contrast, the commercially available collagen/TCP composites exhibit significantly less volume shrinkage after burn-out, that is to say 21% in the case of "Vitoss Foam Strip" and 53% in the case of "Vitoss Foam Pack". The composite material according to the invention contains a higher proportion of collagen. After implantation, the organic component (for example collagen) is absorbed more quickly than the inorganic component in the osseous environment. The greater decrease in the volume of the composite material according to the invention is therefore also associated with more rapid regeneration and accordingly with more rapid success of treatment.

Example 5

2.25 g of constituent Q are mixed with 15 ml of constituent D and heated, with stirring, to 70° C. Once constituent Q has completely dissolved and the solution has cooled to 40° C., first of all 0.0225 g of constituent R and then 13.5 g of the granular fractions 150-500 μm of constituent I and also 1 g of the fraction <150 μm of the same substance are added. The solution is then poured into a mould while still warm and placed in a refrigerator to cool and cross-link. The

TABLE 3

Volume shrinkage of the composite materials according to incineration analysis

| | Volume [cm³] | Weight after burn-out [g] | Tamped density after burn-out [g/cm³] | Volume after burn-out [cm³] | % by volume measured relative to starting volume | Shrinkage in % |
|---|---|---|---|---|---|---|
| CF 33 | 2.18 | 0.57 | 0.79 | 0.72 | 33.0 | 67.0 |
| CF 34 | 2.58 | 0.68 | 0.76 | 0.89 | 34.6 | 65.4 |
| CF 35 | 2.37 | 0.67 | 0.76 | 0.88 | 36.9 | 63.1 |
| CF 36 | 2.51 | 0.63 | 0.73 | 0.87 | 34.6 | 65.4 |
| CF 37 | 2.51 | 0.46 | 0.69 | 0.67 | 26.6 | 73.4 |
| CF 38 | 2.41 | 0.45 | 0.66 | 0.68 | 28.1 | 71.9 |
| CF 39 | 2.00 | 0.34 | 0.67 | 0.50 | 25.0 | 75.0 |
| CF 40 | 2.26 | 0.41 | 0.84 | 0.49 | 21.8 | 78.2 |
| Vitoss Foam Strip | 1.43 | 0.36 | 0.32 | 1.14 | 79.4 | 20.6 |
| Vitoss Foam Pack | 1.74 | 0.32 | 0.39 | 0.82 | 46.9 | 53.1 |

Example 6

1.5 g of constituent Q are mixed with 15 ml of constituent D and heated, with stirring, to 70° C. Once constituent A has completely dissolved, 0.0225 g of constituent R, 20 g of the granular fraction <150 µm of constituent 1 and 2.5 g of the granular fraction 150-500 µm of constituent I are added. Air is then blown into the solution and the foamed material is poured into a mould. For cooling and cross-linking the mould is placed in a refrigerator. The implants can be demoulded after 12 hours. After packaging, sterilisation by gamma rays can be carried out.

Example 7

The granular fraction 150-500 µm and the fraction 1000-4000 µm are separated out from constituent M by sieving and mixed in a ratio of 1:1. 190 g of constituent O are suspended in 1000 ml of constituent D and ground by means of a colloid mill. The mixture of the two granular fractions is added and the mixture is intimately mixed. After addition of 10 ml of constituent B, the mixture is neutralised, poured into a square high-grade steel mould and lyophilised. Depending upon the lyophilisation procedure (slow or fast) it is possible to obtain composite materials having densities of 0.2 or 0.4 g/ml. After packaging, sterilisation by gamma rays can be carried out.

Example 8

The granular fraction 150-500 µm and the fraction 1000-4000 µm are separated out from constituent M by sieving and mixed in a ratio of 1:1. 190 g of constituent O are suspended in 1000 ml of constituent D and ground by means of a colloid mill. The mixture of the two granular fractions is added and the mixture is intimately mixed. After addition of 10 ml of constituent B, the mixture is neutralised, poured into a square high-grade steel mould and lyophilised. Depending upon the lyophilisation procedure (slow or fast) it is possible to obtain composite materials having densities of 0.2 or 0.4 g/ml. After packaging, sterilisation by gamma rays can be carried out.

The invention claimed is:

1. A biologically degradable composite material for bone reconstruction or replacement having an open-porous base structure, characterized in that said composite material is in sterile form and consists of:
   at least one organic component (c);
   an inorganic component;
   and optional additives;
   wherein the inorganic component consists of:
   (i) a first inorganic component (a);
   (ii) a second inorganic component (b); and
   (iii) a third inorganic component (d);
   wherein said first inorganic component (a) is a granular material and each granule has an intragranular porosity of 30-40% by volume, based on the volume of the granule; the second inorganic component (b) is a granular material and each granule has an intragranular porosity of 60-70% by volume, based on the volume of the granule; and the densities of the first inorganic component (a) and the second inorganic component (b) are different; and
   wherein the first inorganic component (a) is present in an amount of 2-20% by weight, based on the composite material; the second inorganic component (b) is present in an amount of 60-78% by weight, based on the composite material; the third inorganic component (d) is present in an amount of 0.1-28% by weight, based on the composite material; and the organic component (c) is present in an amount of 10-20% by weight, based on the composite material, with the proviso that the total amount of the components contained in the composite material is not more than 100% by weight and
   wherein the first inorganic component (a), the second inorganic component (b), and the third inorganic component (d) are in each case a granular material composed of pure-phase beta-tricalcium phosphate having from 0 to 15% by weight of a sodium magnesium silicate glass additive, based on the beta-tricalcium phosphate, or a granular material composed of calcium alkali orthophosphate glass ceramics having from 1 to 15% by weight of a sodium magnesium silicate glass additive based on the calcium alkali orthophosphate glass ceramics; and
   wherein the at least one organic component (c) is collagen; and
   wherein the composite material has a density of from 0.1 to 2 g/cm$^3$ or from 0.2 to 0.4 g/cm$^3$.

2. The biologically degradable composite material of claim 1, wherein the first inorganic component (a) has a bulk density of approximately 0.8-1.5 g/cm$^3$ and the second inorganic component (b) has a bulk density of approximately 0.5-0.9 g/cm$^3$, with the proviso that the bulk density of the second inorganic component (b) is different than that of the first inorganic component (a) and the difference in density is at least 0.1 g/cm$^3$, and wherein the bulk density of the second inorganic component (b) is less than that of the first inorganic component (a).

3. The biologically degradable composite material of claim 1, wherein the first inorganic component (a); or the second inorganic component (b); or the third inorganic component (d); or the first inorganic component (a), and the second inorganic component (b) or the third inorganic component (d); or the first inorganic component (a), the second inorganic component (b) and the third inorganic component (d) contain(s) micropores, mesopores, macropores, or a combination thereof, wherein the micropores, mesopores or macropores interconnect.

4. The biologically degradable composite material of claim 3, wherein the micropores form an interconnecting network into which discrete mesopores and macropores have been introduced in homogeneous distribution.

5. The biologically degradable composite material of claim 1, wherein the first inorganic component (a), the second inorganic component (b), and the third inorganic component (d) are in each case a granular material containing biologically active, polygonal, rounded particles which consist of pure-phase beta-tricalcium phosphate having from 0 to 15% by weight of a sodium magnesium silicate glass additive, based on the beta-tricalcium phosphate; or calcium alkali orthophosphate glass ceramics having from 1 to 15% by weight of a sodium magnesium silicate glass additive based on the calcium alkali orthophosphate glass ceramics.

6. The biologically degradable composite material of claim 1, wherein the first inorganic component (a) is a granular material having particles of a size of 1000-2000 µm; the second inorganic component (b) is a granular material having particles of a size of 150-500 µm; and the third inorganic component (d) is a granular material having particles of a size of 150-500 µm and a total porosity of approximately 50-60% by volume, based on the porosity of the first inorganic component (a) or the second inorganic component (b);

wherein the first inorganic component (a), the second inorganic component (b), and the third inorganic component (d) are in each case a granular material comprising primary particles, wherein said primary particles have a d50 value of at least 10 μm.

7. The biologically degradable composite material of claim 1, wherein the organic component (c) encapsulates the first inorganic component (a), the second inorganic component (b) and the third inorganic component (d); or is contained in and plugs the pores of the first inorganic component (a), the second inorganic component (b), and the third inorganic component (d).

8. The biologically degradable composite material of claim 1, wherein the organic component (c) encapsulates the first inorganic component (a), the second inorganic component (b) and the third inorganic component (d); and is contained in and plugs the pores of the first inorganic component (a), the second inorganic component (b), and the third inorganic component (d).

9. The biologically degradable composite material of claim 1, wherein the organic component (c) and the first inorganic component (a) and second inorganic component (b) are cross-linked.

10. The biologically degradable composite material of claim 1, wherein the additives consist of,
(i) an aqueous solution of a hydrogel-forming substance, the hydrogel-forming substance being selected from modified cellulose, starch, methyl cellulose, carboxymethyl cellulose, hydroxymethyl cellulose, dextran, hyaluronic acid, sodium hyaluronate, polyethylene glycol, or a combination thereof;
(ii) at least one anti-bacterial, wound-healing-promoting, bone-growth-promoting, coagulation-inhibiting substance, or a combination thereof, in pores; on a surface of the composite material; or in pores and on a surface of the composite material; or
(iii) a combination of (i) and (ii).

11. The biologically degradable composite material of claim 1, wherein the composite material has a specific surface area of from 0.1 to 2 m²/g or from 0.2 to 0.4 m²/g.

12. The biologically degradable composite material of claim 1, wherein the composite material has a ratio between density and specific surface area of from 0.1 to 3; from 0.5 to 0.7; or from 1.5 to 2.0.

13. The biologically degradable composite material of claim 1, wherein, according to combustion analysis of the composite material, the composite material has a ratio between density and volume shrinkage of from 0.1 to 1.0; from 0.2 to 0.3; or from 0.5 to 0.7.

14. A method for preparing a composite material of claim 1, comprising:
(i) adding the at least one organic component (c) to a water-containing solution to form a suspension;
(ii) adding the first inorganic component (a), the second inorganic component (b), the third inorganic component (d), and a cross-linking agent to the suspension of (i);
(iii) mixing the components of (ii) to form a solution;
(iv) foaming the solution of (iii) by the introduction of gas or by mechanical manipulation;
(v) transferring the foamed solution of (iv) to a mould and then drying by lyophilization to form the composite material; and
(vi) subjecting the composite material to a heat treatment of 80 to 120° C. for 0.25 to 48 hours; wherein
the composite material is shaped before or after lyophilization or heat treatment.

15. The method of claim 14, wherein the cross-linking agent is an organic acid, or an aqueous or alcoholic solution of an organic acid.

16. The method of claim 14, wherein the first inorganic component (a); or the second inorganic component (b); or the third inorganic component (d); the first inorganic component (a), and the second inorganic component (b) or the third inorganic component (d); or the first inorganic component (a); the second inorganic component (b) and the third inorganic component (d) are in each case a granular material containing biologically active, polygonal, rounded particles which consist of pure-phase beta-tricalcium phosphate having from 0 to 15% by weight of a sodium magnesium silicate glass additive, based on the beta-tricalcium phosphate; or calcium alkali orthophosphate glass ceramics having from 1 to 15% by weight of a sodium magnesium silicate glass additive based on the calcium alkali orthophosphate glass ceramics.

* * * * *